United States Patent [19]

Weng

[11] Patent Number: 5,601,592
[45] Date of Patent: Feb. 11, 1997

[54] MECHANICAL LIFT SYSTEM FOR SURGERY

[76] Inventor: Edward E. Weng, 51077 Sand Shores, Shelby Township, Macomb County, Mich. 48316

[21] Appl. No.: 368,983

[22] Filed: Jan. 5, 1995

[51] Int. Cl.⁶ ............................................. A61M 29/00
[52] U.S. Cl. ............................................. 606/198
[58] Field of Search ............................ 212/97; 135/15.1, 135/98, 99, 158; 600/201, 204, 206, 214, 219, 235; 606/1, 108, 127, 167, 184, 185, 190–198; 604/164, 264; 211/16, 119.1; 68/240; 248/317

[56] References Cited

U.S. PATENT DOCUMENTS

| | | | |
|---|---|---|---|
| 5,176,128 | 1/1993 | Andrese | 600/206 |
| 5,279,564 | 1/1994 | Taylor | 606/198 |
| 5,312,417 | 5/1994 | Wilk | 606/127 |
| 5,318,012 | 6/1994 | Wilk | 606/198 |

Primary Examiner—Glenn Dawson
Attorney, Agent, or Firm—Howard & Howard

[57] ABSTRACT

A mechanical lift system for use in laparoscopic surgery includes a plurality of suspension members which support the abdominal wall such that the abdominal wall may be mechanically lifted to create a cavity for the scope and the laparoscopic surgery. The suspension members preferably allow bending movement in a first direction, which will be vertically upwardly during the surgical operation, but restricts bending movement in the opposed direction. In this way, the suspension members allow bending movement to conform to the shape of the abdominal wall, but will restrict any such bending movement when the abdominal wall is being lifted by the suspension members. In one preferred embodiment, the suspension members include a flexible strap with a plurality of blocks placed on one face of the strap. When the suspension member is bent with the strap moving away from the blocks, bending is allowed. However, if there is a force tending to bend the straps in a direction toward the blocks, spaced surfaces of the blocks come into contact, preventing further bending movement.

22 Claims, 2 Drawing Sheets

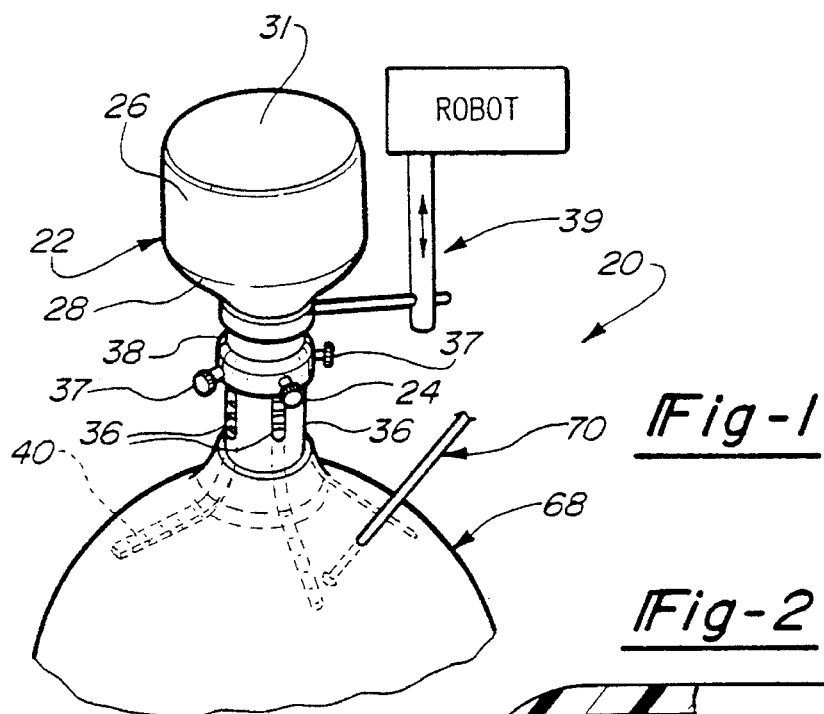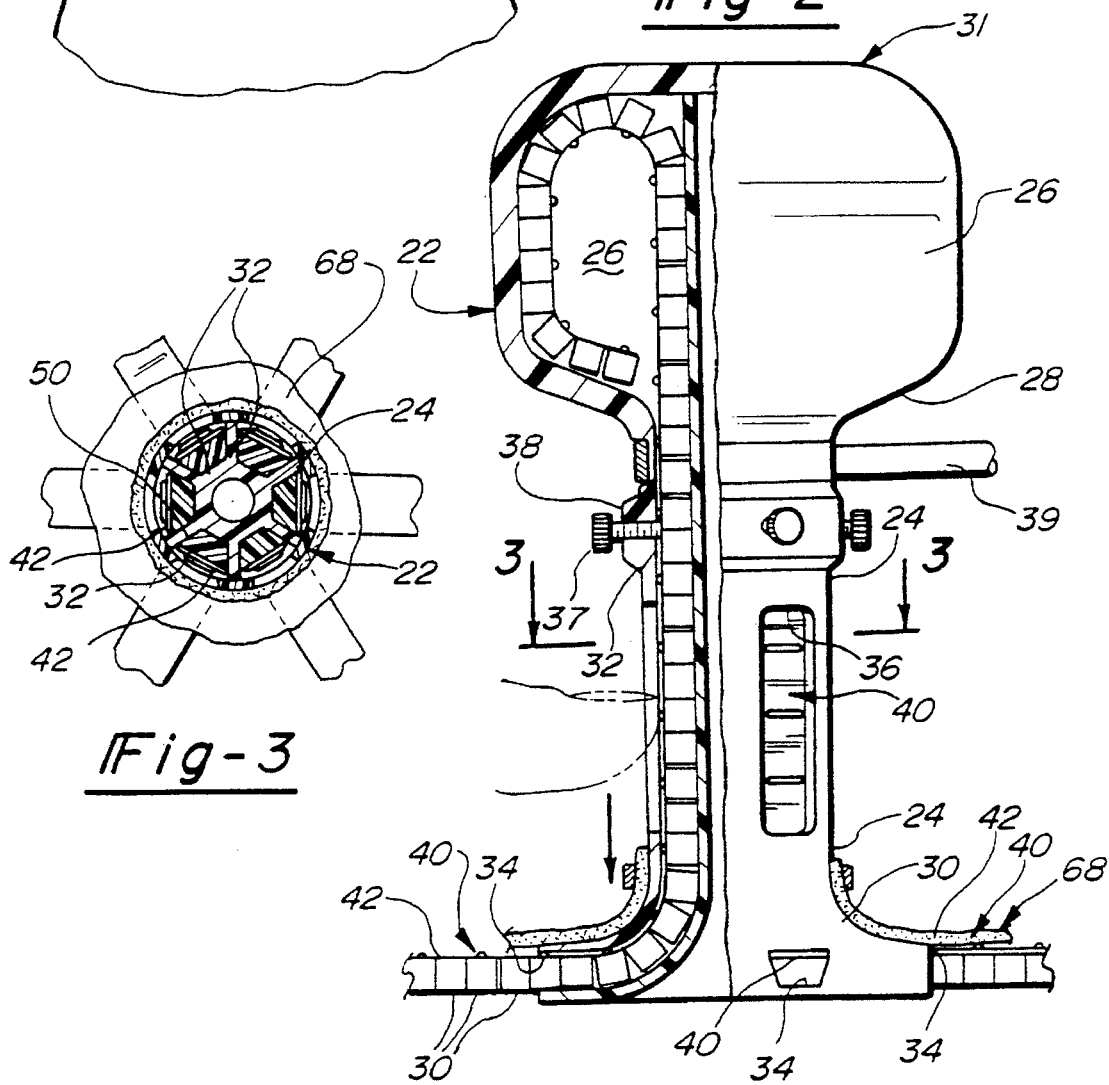

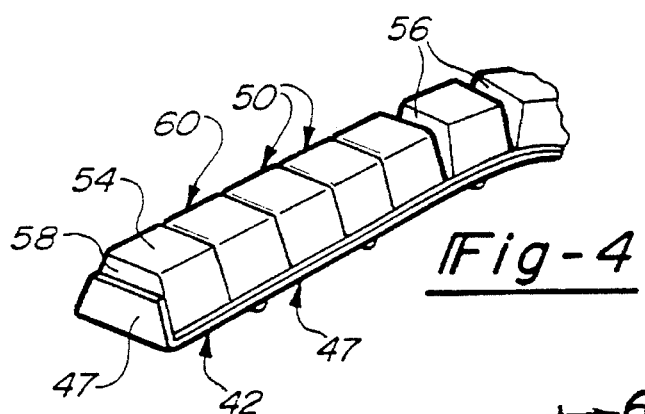
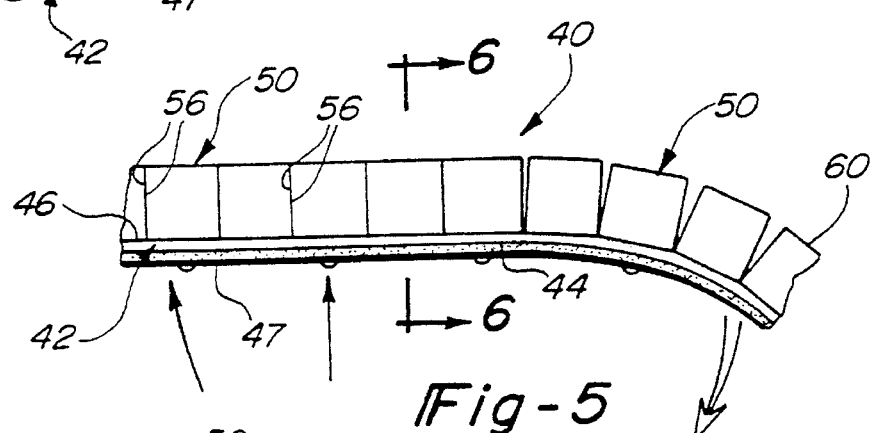
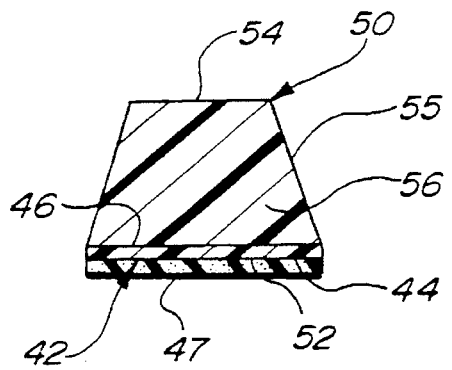
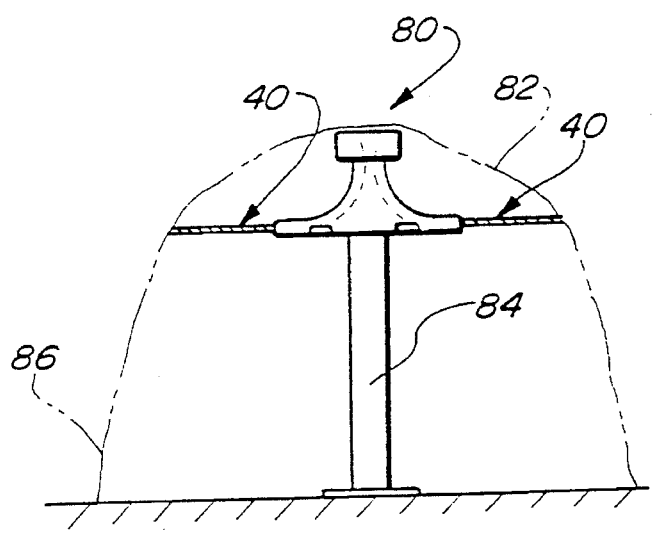
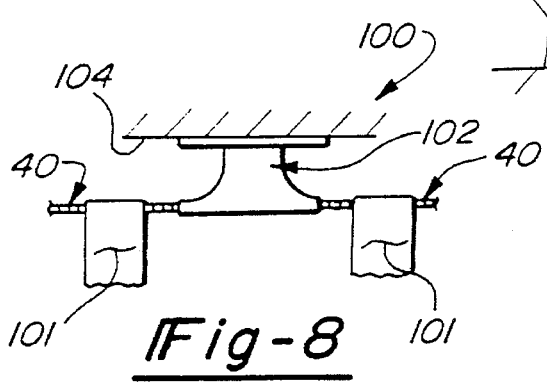

MECHANICAL LIFT SYSTEM FOR SURGERY

BACKGROUND OF THE INVENTION

The present invention relates to a mechanical lift system which is particularly useful in performing laparoscopic surgery.

One of the newest types of surgical procedures is laparoscopic surgery. In such procedures several small incisions are made in a patient. A scope is inserted through one of those incisions and monitors the surgery. Surgical tools are inserted through the other incisions. By inserting a scope within the patient to monitor the surgical area, the surgeon is able to perform the surgery without making the otherwise necessary large incision to provide access to the area of the surgery. The use of such surgery has a great potential for many surgical procedures. The patient recovers much more quickly from the small incisions than the otherwise required large incisions.

In one standard laparoscopic surgery, gas is inserted into the patient's abdomen to inflate the abdomen and create a space for the scope to view the area to be treated in the surgery. The surgeon monitors the surgery on a video screen by watching a video provided by the internal scope. Surgical tools extend into the patient and perform the surgery remotely with the surgeon being guided by the video.

However, the use of gas to inflate the abdomen has several drawbacks. It is necessary that each of the incisions for the surgical tools be sealed against air leakage. Sheaths are typically inserted through each incision and the surgical tools are slid within the sheath and into the patient. The sheaths are necessarily of small diameter; and since the surgical tools must extend through the sheath, the surgical tools are also of a very small diameter. Further, the use of lasers in surgery creates smoke within the abdominal cavity. This smoke interferes with the surgeon's view of the procedure through the internal scope. It is difficult to remove the smoke or steam while maintaining an inflated abdomen.

Typically, the removal of smoke requires suction, which also removes the gas from the abdomen, causing collapse of the abdomen.

Moreover, it is often the case that the sheaths leak some air. As air leaks outwardly of the abdominal cavity, the abdomen collapses.

When the abdomen collapses, the scope is unable to provide an adequate image to the surgeon. The surgeon must thus correct the leak or in the case of smoke removal, complete the smoke removal, and then wait for the abdomen to be reinflated before continuing with surgery. Obviously, such delays are undesirable.

To replace the standard gas inflation, it has been proposed to utilize certain mechanical support structures. As an example, it has been proposed to utilize a pair of flexible wires formed into a cross to support the abdomen. In addition, the use of a rigid rod has also been disclosed. There are problems with any of these types of mechanical support systems. On one hand, the support system cannot be unduly rigid, or it could damage the abdominal wall. Further, the support system must be able to adequately support the abdominal wall without allowing the unsupported portions between the mechanical portions to droop downwardly. The prior mechanical support systems have not adequately provided these combined requirements.

SUMMARY OF THE INVENTION

The present invention provides a mechanical lift system which is particularly useful for laparoscopic surgery. Because the present invention does not require inflation of the abdomen, the problems of maintaining an airtight seal and removing smoke are overcome. The mechanical lift system generally comprises a main body which is generally cylindrical and includes a lower flanged portion having a plurality of apertures. The main body further includes a plurality of circumferentially-spaced axial channels which curve outwardly within the lower portion and terminate at the apertures in the lower portion. The channels are generally perpendicular to the main body at the apertures.

The mechanical lift system further includes a plurality of suspension members, which slide within the channels and through the apertures. Broadly speaking, the suspension members consist of structures which have freedom to bend in a first direction perpendicular to the axis of the suspension members, but which are more resistant to bending movement in the opposed direction. The suspension members are preferably positioned such that they can bend to conform to the shape of the abdomen, but their resistant side is positioned such that when lifting the abdominal wall, they will not bend, thus fully supporting the wall and providing a cavity. The surgeon is thus provided with an adequate cavity and an adequate image for the surgery.

Preferably, the suspension members comprise a plurality of blocks hingeably connected by an elongated strap. The blocks each have a first surface, an opposite second surface, and two opposite lateral surfaces. The first surfaces of the blocks are secured to the strap so that adjacent blocks have facing lateral surfaces. The straps are bendable away from the blocks, but are not bendable toward the blocks past the point where the lateral surfaces of adjacent blocks make contact. It is this feature which provides the benefits mentioned above.

The suspension members are slidably disposed within the channels so that the strap is toward the outside of the main body. The suspension members bend and follow the curve of the channel and extend from the lower portion of the main body. Once extended, the suspension members engage the abdominal wall, allowing lifting. With the suspension members engaging the abdominal wall, the abdominal wall imparts a force downward on the strap side of the suspension members, thereby imparting a force on the attached blocks. After minimal bending, the lateral surfaces of adjacent blocks contact, preventing the suspension members from bending. However, the strap can bend upwardly to conform to the shape of the abdomen. In this way, it is ensured that the strap does fully conform to the surface of the abdomen and that the plural suspension members will fully support the abdominal wall when lifted.

A lifting mechanism, such as a robot, is utilized to lift the mechanical lift system after the suspension members have been extended within the abdomen. In one proposed embodiment, there are six suspension members which are spaced circumferentially about a central axis of the mechanical lift system. When the suspension members are extended, they fully support the abdominal wall such that the lift system can be lifted and a cavity is created into which a surgeon can insert a scope for monitoring the surgery.

The inventive lift system also has non-medical uses. Disclosed examples include the use of the system as supporting a tent, or as providing a rack for holding items, such as towels.

BRIEF DESCRIPTION OF THE DRAWINGS

The above, as well as other advantages of the present invention, will become readily apparent to those skilled in the art from the following detailed description of a preferred embodiment when considered in the light of the accompanying drawings in which:

FIG. 1 is a perspective view of a mechanical lift system in accordance with the present invention inserted into the abdominal wall of a laparoscopic surgery patient;

FIG. 2 is a side view, partially broken away of the mechanical lift system of FIG. 1, with a suspension member being extended manually;

FIG. 3 is a sectional view along line 3—3 of FIG. 2;

FIG. 4 is a perspective view of a suspension member;

FIG. 5 is a side view of the suspension member of FIG. 4;

FIG. 6 is a sectional view along line 5—5 of FIG. 5;

FIG. 7 is another embodiment of the mechanical lift system of the present invention;

FIG. 8 is another embodiment of the mechanical lift system of the present invention.

DESCRIPTION OF THE PREFERRED EMBODIMENT

A mechanical lift system 20 in accordance with the present invention is shown in FIG. 1. Mechanical lift system 20 includes a main body 22 having a trunk 24 and an upper chamber 26. The main body 22 can be stainless steel, plastic, or other suitable material. The trunk 24 is preferably generally cylindrical and has an axis. As shown in FIG. 2, the trunk 24 includes an upper flanged portion 28 which is continuous with the upper chamber 26 and a lower flanged portion 30. A cap 31 is snap-fit or otherwise removably secured over the upper chamber 26. Channels 32 curve outwardly within the lower portion 30 until approximately perpendicular to the axis of the trunk 24, at which point each channel 32 terminates in an aperture 34 in the lower portion 30. Each of the channels 32 extends into the upper chamber 26.

As shown in FIG. 3, a plurality of axially-extending channels 32 are disposed peripherally about the axis of the trunk 24. The channels 32 are preferably trapezoidal in transverse section and extend the length of the trunk 24.

As can be seen in FIGS. 1 and 2, the trunk 24 of the main body 22 includes an orifice 36 opening into each channel 32. The trunk 24 also includes a screw 37 threaded in an aperture 38 extending into each channel 32. A robot arm 39 or other lifting means is secured to the main body 22 below the upper flanged portion 28 of the trunk 24. Suspension members 40 are received in each channel 32.

As can best be seen in FIGS. 4–6, a plurality of suspension members 40 each include an elongated strap 42 having a first surface 44 and an opposite second surface 46. The straps 42 are preferably flexible but resistant to stretching longitudinally. The straps can be made from reinforced polyethylene or other suitable material. A foam layer 47 having a plurality of longitudinally-spaced ribs 48 may be placed on the first surface 44 of the strap 42.

As shown in FIG. 6, each suspension member 40 includes a plurality of blocks 50 attached to a strap 42. Each block 50 has a generally flat first surface 52, an opposite second surface 54, and two opposing outer surfaces 55. Each block has a pair of lateral surfaces 56 facing an adjacent block. The first surface area 52 is preferably greater than the second surface area 54, thereby making the lateral surfaces 56 generally trapezoidal in shape. The first surface 52 of each block 50 is secured to the second surface 46 of the strap 42 and oriented so that adjacent blocks 50 have facing lateral surfaces 56. The foam layer 47 may extend over the leading lateral surface 58 of the first block 60.

As can be seen at the left side in FIG. 5, the blocks 50 prevent the strap 42 from bending toward the blocks 50, since lateral surfaces 56 contact, preventing further bending. As shown at the right side of FIG. 5, the strap 42 may bend away from the blocks 50. This bending allows storage and also allows the suspension to move through the small incision, then bend as required to conform to the abdominal wall. The first surfaces 52 of adjacent blocks 50 are hingeably connected by the strap 42 so that the abutting lateral surfaces 56 of adjacent blocks 50 restrict the range of motion of the suspension member 40.

Adjacent blocks 50 are preferably spaced slightly. Alternatively, the lateral surfaces 56 of selected blocks 50 can be sloped inward. By varying the spacing between selected adjacent blocks 50 or sloping the lateral surfaces 56 of selected blocks 50 inward, the suspension member 40 can also limit bending at certain portions to fit the shape of the abdominal wall.

Referring to FIGS. 1 and 2, initially the suspension members 40 are stored inside the main body 22. Each suspension member 40 is slidably disposed within a channel 32 in the main body 22, with the excess of the suspension member 40 coiled within upper chamber 26. Upper chamber 26 is accessible by removing the cap 31. The lower portion 30 is inserted into a incision in the abdominal wall 68 of a patient. The flesh of the patient, including the abdominal wall 68, is obviously much more complex than is shown in FIG. 2. The drawing is simplified to focus on the inventive aspects. Each suspension member 40 is then pushed through a channel 32 by pushing downward on the strap 42, which can be accessed through the orifices 36 in the trunk 24. The suspension members 40 exit the main body 22 through the apertures 34 in the lower portion 30 and extend radially outwardly of the main body 22 inside the abdominal wall 68. The fact that the surgeon is able to move the suspension members downwardly by his finger, provides the surgeon with touch or "feel" such that the surgeon does not force the suspension members unduly and injure the patient. A surgeon may easily and slowly insert the suspension members, with the suspension members bending slightly as required to conform to the abdominal wall. When the suspension members 40 have been fully extended such that they will provide adequate support for lifting the abdominal wall 68, the screws 37 are tightened, thereby locking the suspension members 40 in the channels 32. A robot arm 39 or other lifting means is secured to the upper flanged portion 28 of the main body 22. The robot arm 39 may lift the main body 22, the suspension members 40, and the abdominal wall 68. A foam layer 47 may provide a cushion for the abdominal wall 68, reducing damage to the abdominal wall 68.

Should any tendency to bend the suspension members 40 occur during lifting, only limited bending will be allowed. Once the lateral surfaces 56 of the blocks come into contact, no further bending is allowed. Moreover, since six spaced suspension members 40 are utilized, adequate support of the entire abdominal wall will be provided. There will not be a tendency to have portions between the support members drooping downwardly, thus reducing the volume of the cavity. The scope can thus provide an adequate image of the surgical area to the surgeon. Because the abdominal wall 68 is not supported by air pressure, it is not necessary that the scope 70 and other surgical tools maintain an airtight seal with the abdominal wall 68. Further, any smoke created by lasers used in the surgery can be removed without deflating and collapsing the abdominal wall 68.

Although the present invention has been described in the context of a lift for use in laparoscopic surgery, it should be apparent that the mechanical lift system could be used in other applications requiring lifting, hanging, or the like. A mechanical lift system 80, according to another embodiment of the present invention, is shown in FIG. 7. The mechanical lift system 80 includes a main body 82 having plurality of suspension members 40 mounted on a post 84. The mechanical lift system 80 provides a support/br fabrics or flexible materials 86, such as a tent. The suspension members 40 extend to a desired length and can be stored within the main body 82 when not in use.

A mechanical lift system 100 according to another embodiment of the present invention is shown in FIG. 8. The mechanical lift system 100 includes a main body 102 which can be mounted on a ceiling 104 or wall. The suspension members 40 can be used to hang or support items, such as towels 101 or lights, plants, tools, etc. The suspension members 40 can be extended to a desired length and can be stored within the main body 82 when not in use.

In accordance with the provisions of the patent statutes, the present invention has been described in what is considered to represent its preferred embodiment. However, it should be noted that the invention can be practiced otherwise than as specifically illustrated and described without departing from its spirit or scope.

What is claimed is:

1. A mechanical lift system comprising:

a main body having an axis and a plurality of axial channels, said main body further having an aperture at one end of each said channel, said channels curving outwardly at a point adjacent said apertures;

a plurality of suspension members slidably disposed within said channels, said suspension members being slidable through said channels, said suspension members being extendable and retractable through said apertures in said main body, each of said suspension members having means thereon for allowing bending of said suspension members in a first direction generally parallel to said axis, but resisting bending of said suspension members in a second direction opposed to said first direction.

2. The system according to claim 1, wherein said main body includes a lower flanged portion, said apertures in said main body being in said lower flanged portion.

3. The system according to claim 1, wherein each of said suspension members comprise a plurality of hingeably connected blocks.

4. The system according to claim 3, wherein a strap connects said plurality of blocks.

5. The system according to claim 4, wherein said first direction is a direction bending said strap away from said blocks, and said second direction is a direction bending said strap toward said blocks, bending in said second direction being restricted by opposed facing sides of said blocks coming into contact.

6. The system as recited in claim 5, wherein said blocks are generally trapezoidal in cross-section.

7. The system according to claim 5, wherein lateral surfaces of said blocks are generally parallel.

8. The system according to claim 1, wherein said blocks are generally trapezoidal in cross-section.

9. The system according to claim 1, wherein said main body includes an enlarged storage chamber above said axial channels, said suspension members being rolled for storage within said storage chamber.

10. The system as recited in claim 1, wherein said mechanical lift system supports a tent attached to ends of said suspension members.

11. The system as recited in claim 1, wherein said mechanical lift system supports several consumer items on said suspension members.

12. The system as recited in claim 11, wherein said consumer items are sheets.

13. A mechanical lift system for use in laparoscopic surgery comprising:

a main body having a trunk and an upper chamber, said trunk having an axis and a lower portion, said trunk having a plurality of channels disposed circumferentially about said axis, said channels extending the length of the trunk, said channels curving outwardly of said trunk within said lower portion until generally perpendicular to said axis of said trunk, each said channel terminating in an aperture in said lower portion, said upper chamber being continuous with said channels;

a plurality of suspension members slidably disposed within said channels, each suspension member comprising:

an elongated flexible strap having a first surface and an opposite second surface;

a plurality of blocks, each said block having two opposite lateral surfaces and a first surface, said first surface of each said block secured to said second surface of said strap, said blocks oriented such that adjacent blocks have adjacent lateral surfaces; and said suspension members being extendable and retractable through said apertures in said lower portion of said main body.

14. The system as recited in claim 13, wherein there are six of said suspension members.

15. The system as recited in claim 13, wherein an aperture is provided extending from an outer surface of said trunk into one of said channels, said aperture providing access to one of said suspension members such that an operator may manually move said suspension member outwardly of said channel into a patient during surgery.

16. The system as recited in claim 13, wherein said suspension members being bendable in a first direction, but being more resistant to bending in a second direction opposed to said first direction, said first direction includes the bending of said straps away from said blocks, and said second direction includes the bending of said strap toward said blocks, said lateral surfaces of adjacent ones of said blocks coming into contact during bending in said second direction, restricting further bending.

17. The system as recited in claim 13, wherein said first surface of said strap is adapted to face the abdominal wall of a patient during surgery.

18. A system as recited in claim 13, wherein said first surface of said strap is spaced radially outwardly relative to said second surface when said suspension member is within one of said channels.

19. The system as recited in claim 13, wherein said strap is provided on said first surface with a relatively soft coating.

20. A method for performing laparoscopic surgery comprising the steps of:

making an incision in an abdominal wall in a patient;

providing a main body having a lower portion for insertion into said incision in a patient, said main body having a plurality of apertures at said lower portion;

providing a plurality of suspension members slidably disposed within said main body, said suspension members being bendable throughout a limited range of motion, said suspension members being extendable and retractable from said main body through said apertures in said lower portion;

inserting said lower portion of said main body into said incision in said abdominal wall of said patient;

extending said suspension members from said main body inside said abdominal wall of said patient; and lifting said main body and suspension members, thereby lifting said abdominal wall of said patient creating a cavity therein.

21. A method as recited in claim 20, wherein said suspension members are provided such that they allow bending movement in a direction vertically upwardly but restrict bending movement in a direction vertically downwardly such that they fully support the abdominal wall of the patient during said lifting.

22. A method as recited in claim 20, wherein said main body is provided with access apertures to allow access to said suspension members within said main body, and further comprising manually moving said suspension members relative to said main body for moving said suspension members into the patient through said apertures.

* * * * *